US005859327A

United States Patent [19]
Dev et al.

[11] Patent Number: 5,859,327
[45] Date of Patent: Jan. 12, 1999

[54] ELECTROPORATION-MEDIATED MOLECULAR TRANSFER IN INTACT PLANTS

[75] Inventors: S. B. Dev, San Diego, Calif.; Yasuhiko Hayakawa, Ichikawa, Japan

[73] Assignee: Genetronics, Inc., San Diego, Calif.

[21] Appl. No.: 517,914

[22] Filed: Aug. 22, 1995

[51] Int. Cl.$^6$ .......................... C12N 15/29; C12N 15/82; C12N 15/00; A01H 4/00
[52] U.S. Cl. .................. 800/205; 435/172.1; 435/172.3; 435/173.6; 435/419
[58] Field of Search .............................. 435/172.1, 172.3, 435/173.6, 240.4, 240.49, 419; 800/205

[56] References Cited

U.S. PATENT DOCUMENTS

| | | | |
|---|---|---|---|
| 5,236,835 | 8/1993 | Mouneimne et al. | 435/173.6 |
| 5,371,003 | 12/1994 | Murry et al. | 435/172.3 |
| 5,384,253 | 1/1995 | Krzyzek et al. | 435/172.3 |

FOREIGN PATENT DOCUMENTS

WO93/21335  10/1993  WIPO.

OTHER PUBLICATIONS

Chowrira, et al., Electroporation–Mediated Gene Transfer into Intact Nodal Meristems In Planta, *Molecular Biotechnology,* vol. 3, No. 1, pp. 17–23, Feb. 1995.

Songstad, et al., Transient expression of GUS and anthocyanin constructs in intact maize immature embryos following electrporation, *Plant Cell, Tissue and Organ Culture,* 33: pp. 195–201, 1993.

Vani Akella and Paul F. Lurquin, Expression in Cowpea seedlings of chimeric transgenes after electroporation into seed–derived embryos, *Plant Cell Reports,* 12: pp. 110–117, 1993.

Senaratna, et al., Direct DNA uptake during the imbibition of dry cells, *Plant Science,* 79: pp. 223–228, 1991.

Dekeyser, et al., Transient Gene Expression in Intact and Organized Rice Tissues, *The Plant cell,* vol. 2, pp. 591–602, Jul. 1990.

Xie et al 1990 Biophys. J. 58:897–903.

*Primary Examiner*—Douglas W. Robinson
*Assistant Examiner*—Thomas Haas
*Attorney, Agent, or Firm*—Fish & Richardson, P.C.

[57] ABSTRACT

A method for producing a genetically modified plant by introducing a polynucleotide to an intact plant or plant cell(s) via electroporation, in the absence of cell wall-degrading enzymes. Genetically engineered plants produced by the method of the invention are also provided. The invention also provides a method for producing a polypeptide in an intact plant cell, including plant tissue or a whole plant by introducing a biologically active polypeptide directly into the plant.

30 Claims, 5 Drawing Sheets

ELECTROPORATION-MEDIATED MOLECULAR TRANSFER IN INTACT PLANTS

BACKGROUND OF THE INVENTION

1. Field of the Invention

This invention relates generally to the transfer of molecules into a plant, and specifically to a method of introducing molecules such as polypeptides or polynucleotides into an intact plant or plant tissue using electroporation.

2. Description of Related Art

The ability to alter the genetic composition of a living cell by transformation is one of the core technologies in biotechnology. By manipulating the genetic repertoire of a cell, one can produce large amounts of a desirable protein product. One of the primary limitations to the alteration of cells has been the technology to carry out the transformation.

Genetically engineered plants are useful for the production of vaccines against human diseases, ranging from tooth decay to life-threatening infections such as bacterial diarrhea, cholera, and AIDS. It may even be possible to produce vaccines in plants which are then eaten as part of the normal diet. Such vaccines might be cheaper than those now available, because plants are easier to grow in large quantities than are the cultured animal cells which are currently being used to make most vaccines.

Most commonly, DNA transfer into plant cells has been accomplished by preparation of protoplasts which are subsequently treated with a DNA-containing solution which is taken up by the protoplast. As plant regeneration from protoplasts has generally been limited to a relatively small number of genotypes for various species, it has been difficult to develop a generally effective protoplast based procedure. Therefore, other approaches have been recently explored.

Typically, means for delivery of DNA into living cells include cellular uptake of DNA precipitates, microinjection of DNA into a single cell, electrofusion, insertion of DNA into cells by micro-projectiles coated with DNA, and cellular uptake of DNA from the surrounding solution following exposure of the cell to a strong electric pulse (i.e., electroporation).

Micro-injection of DNA into single cells is inefficient and tedious, and only a limited number of cells can be treated at one time. Electro-fusion is a means by which exogenous genetic material is introduced into a host plant (U.S. Pat. No. 4,832,814). The insertion of genetic material is accomplished by either permeabilizing the cell membrane to allow entry of genetic material or fusing the host cell with a cell containing the genetic material of interest. Electro-fusion has many limitations and does not work for all plant cells (see U.S. Pat. No. 4,822,470).

Insertion of DNA into cells using DNA-coated micro-projectiles (U.S. Pat. No. 4,945,050) has also been utilized for genetically modifying plants. The exposure to gas and debris from an explosive event arises from the need to use an explosion to achieve the high degree of acceleration required to give the micro-projectiles the requisite kinetic energy to pierce the cell. These conditions impose severe limitations to applying the projectile method to cells in an intact plant or organism. The high velocity ballistic penetration by small particles with the nucleic acid either within the matrix of small beads or particles, or on the surface (Klein, et al., *Nature*, 327:70, 1987). Although, typically only a single introduction of a new nucleic acid segment is required, this method particularly provides for multiple introductions. However, this technology requires that plants go through a tissue culture stage, and again the conditions for regeneration of whole plants from plant cells are not without problems.

Cellular uptake of DNA following exposure of the cell to an electric pulse is accomplished often in surroundings which are not too far from physiological, and often for an amount of time on the order of milliseconds or less. The target cells are typically required to be placed in a cavity (e.g., a cuvette). Most electro-transformation is carried out on cells in suspension after dissociating the tissue to single cells or small aggregates of cells before treating.

Direct transfer of genes into cells or intact plant leaves or tissues by electroporation, has required the addition of chemicals such as spermine, spermidine or lipophilic molecules such as Lipofectin® (see for example, U.S. Pat. No. 5,286,634). Most recently, Chowrira, et al. (*Molecular Biotechnology*, 3:17, 1995) showed studies which demonstrated that leguminous plants could be transformed by electroporation of DNA into intact nodal meristems in planta, resulting in transient expression and stable integration of transgenes, when DNA is first mixed with lipofectin reagent. The study showed that the amount of lipofectin added to the plasmid DNA was critical for the introduction of DNA to the plant cells.

Transient expression of gus gene (β-glucuronidase) and anthocyanin was obtained in immature embryos by electroporation of DNA in a spermidine-containing electroporation solution (Songstad, et al., *Plant Cell Tissue and Organ Culture*, 33:195, 1993). NPTII (neomycin phosphotransferase II) gene expression was also greatly enhanced by transformation of DNA in buffer containing spermidine, which delays lysis of protoplasts and inhibits the activity of nucleases (Dekeyser, et al., *The Plant Cell*, 2:591, 1990). In contrast, transformation in the absence of spermidine resulted in extremely low if any gene expression. Spermine and lipofectin containing buffers were also utilized for transferring DNA via electroporation to intact cowpea seed-derived embryos (Akella and Lurquin, *Plant Cell Reports*, 12:110, 1993).

Monocot cells were transformed in the absence of cell wall degrading enzymes by electroporation of either single cell suspensions or cell aggregates, both from prior dissociation of plant tissue (Gobel, et al., WO93/21335). Therefore, in vitro cell culture was required following treatment.

There remains a need for a method of introducing molecules into plants which avoids the problems associated with regeneration from protoplasts and which allows many cells to be transformed at one time, in the absence of chemicals.

SUMMARY OF THE INVENTION

The present invention is based on the seminal discovery that molecular transfer to an intact plant or plant tissue can be accomplished by electroporation of the plant or plant tissue, in the absence of chemical treatment (e.g., lipophilic or polycationic compounds), and without dissociation of plant tissue. The invention provides a method for introducing a polynucleotide into a plant, which is expressed once introduced into the plant. The invention also provides a method for introducing a biologically active polypeptide into the plant.

In a first embodiment, the invention provides a method of producing a genetically modified plant comprising contacting an intact plant cell(s) with a polynucleotide, applying an electrical impulse(s) via electroporation to the plant cell(s), under conditions and for sufficient time to allow uptake of the polynucleotide and expressing the polynucleotide in the plant cell(s).

In another embodiment, the invention provides a method for producing a heterologous polypeptide in an intact plant cell(s) comprising contacting the plant cell(s) with the polypeptide to be introduced, wherein the introduced polypeptide is biologically active, applying an electrical impulse via electroporation to the plant cell(s), under conditions and for sufficient time to allow uptake of the polypeptide and recovering the polypeptide from the plant cell(s).

In yet another embodiment, the invention provides a method of modulating gene expression in an intact plant cell(s), comprising contacting the plant cell(s) with a modulatory amount of polynucleotide, applying an electrical impulse(s) via electroporation to the plant cell(s), under conditions and for sufficient time to allow uptake of the polynucleotide, and modulating gene expression in the plant. Examples of such modulatory polypeptides include antisense, triplex agents and ribozymes.

BRIEF DESCRIPTION OF THE DRAWINGS

FIG. 1A, shows the intact leaf.

FIG. 2A shows the portion of the leaf to be treated is shown; FIG. 2B shows the pincer electrodes; FIGS. 2C, 2D, and 2E show treatment of the leaf section with the electrodes.

DETAILED DESCRIPTION OF THE INVENTION

Figure 1A:
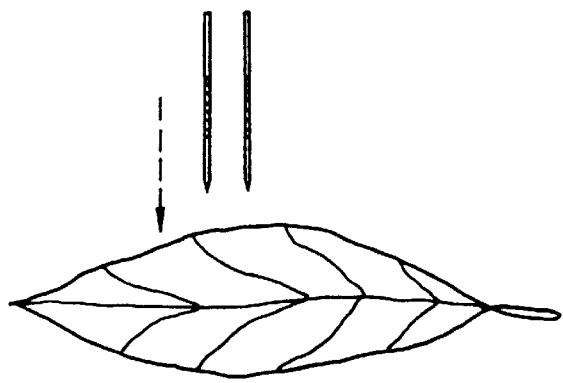
FIGS. 1A, B, C, and D shows a schematic illustration for introduction of polypeptide into an intact leaf using needle electrodes.
Figure 1B:
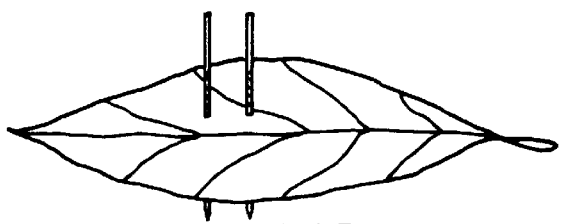
FIG. 1B, shows insertion of the needles into the intact leaf.
Figure 1C:
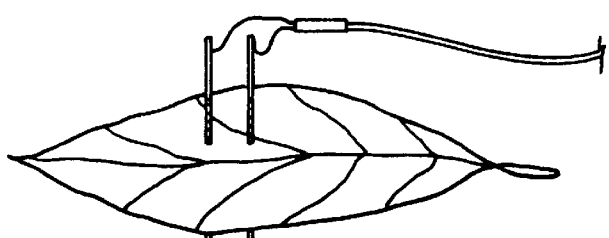
FIG. 1C, shows attachment of the generator to the needles.
Figure 1D:
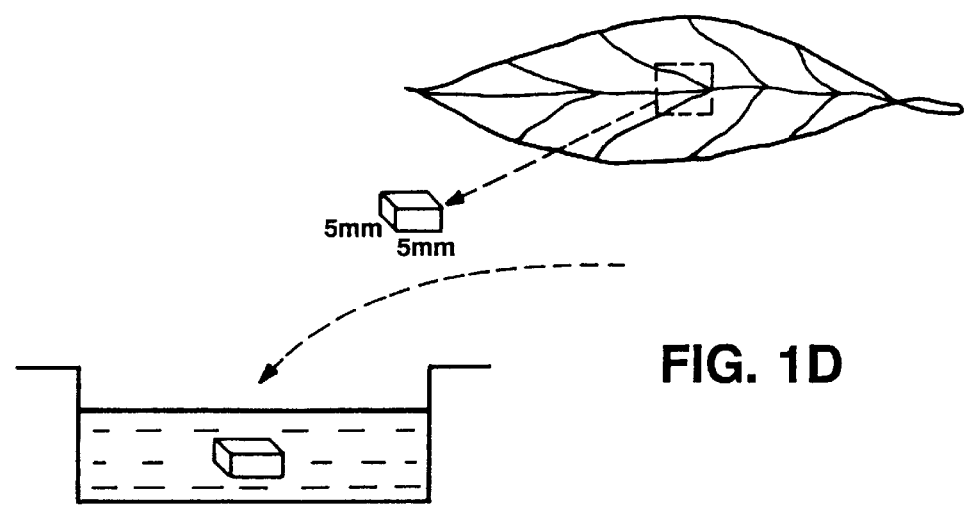
FIG. 1D, shows excision of a section of the transfected leaf.
Figure 2A:
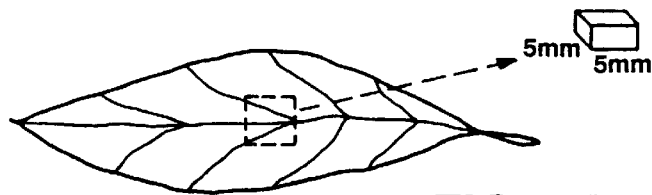
FIGS. 2A–E shows a schematic illustration for introduction of polypeptide into an intact leaf using pincer electrodes.
Figure 2B:
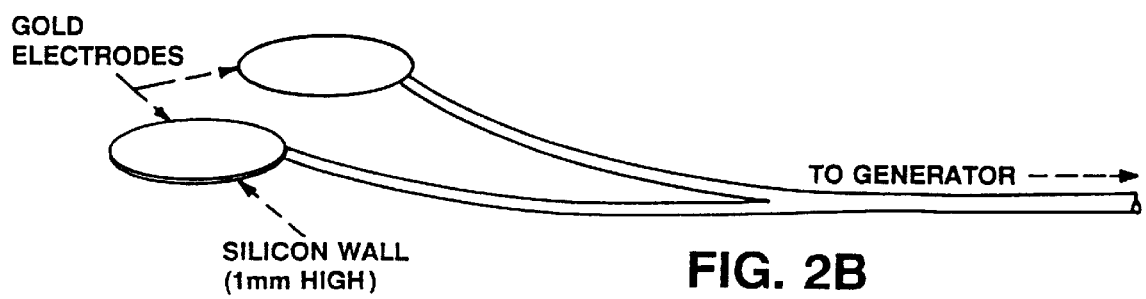
Figure 2C:
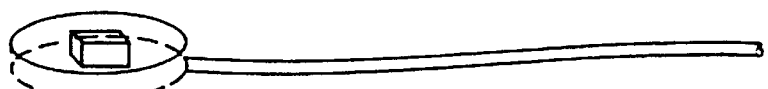
Figure 2D:
Figure 2E:
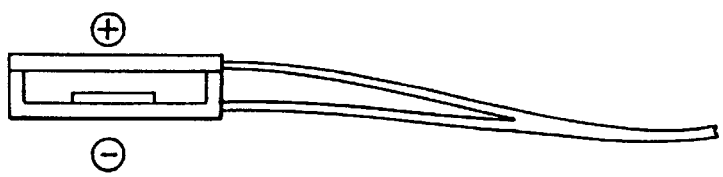
Figure 3A:
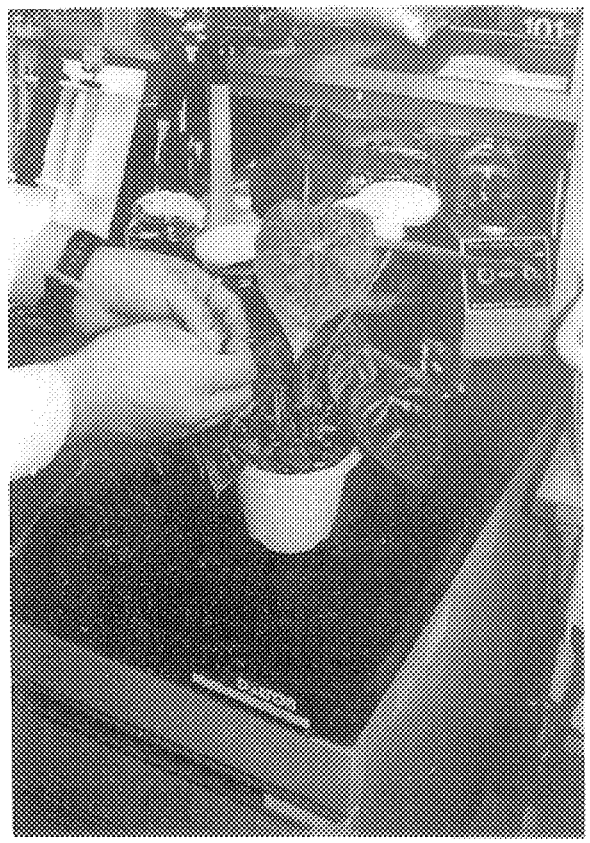
FIG. 3a shows direct gene transfer of whole, intact plants via electroporation.
Figure 3B:
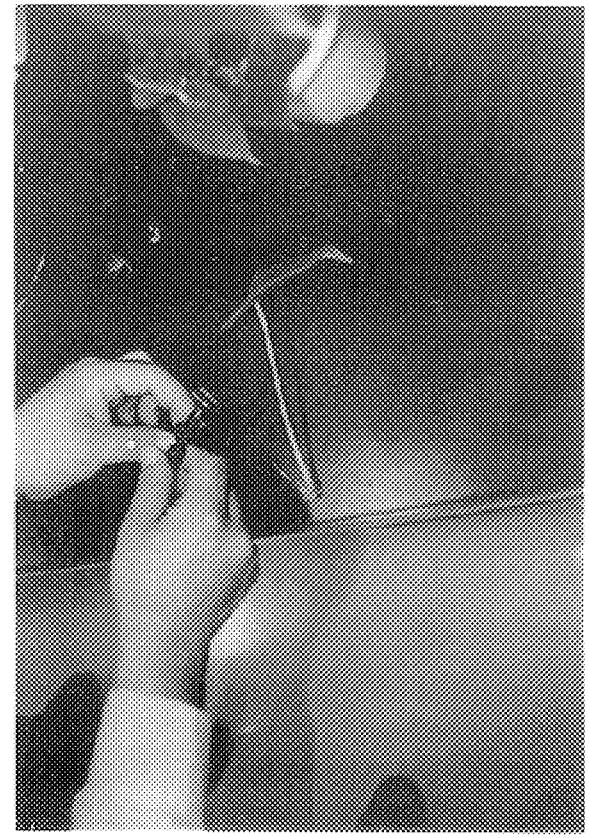
FIG. 3b shows direct gene transfer of whole, intact plants via electroporation.
Figure 3C:
FIG. 3c shows direct gene transfer of whole, intact plants via electroporation.
Figure 3D:
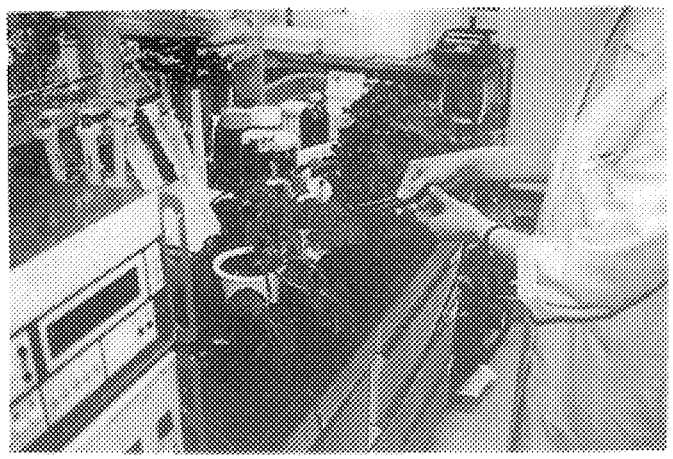
FIG. 3d shows direct gene transfer of whole, intact plants via electroporation.
Figure 3E:
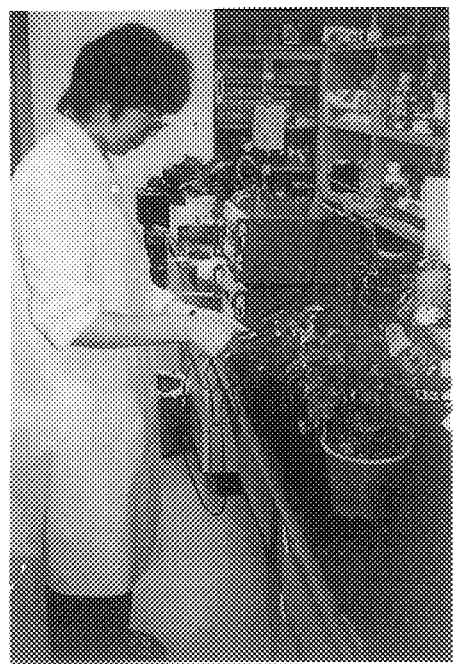
FIG. 3e shows direct gene transfer of whole, intact plants via electroporation.

The present invention arose out of the discovery that molecules can be introduced into plant cells by electroporation in the absence of prior enzymatic treatment to the cells and without dissociating the plant tissue into single cell or cell aggregate suspensions. The molecules, including polynucleotides and polypeptides, are introduced to the plant in a physiological buffer without lipophilic or polycationic substances.

In a first embodiment, the invention provides a method of producing a genetically modified plant comprising contacting an intact plant cell(s) with a polynucleotide wherein the polynucleotide is operably associated with a promoter, applying an electrical impulse(s) via electroporation to the plant cell(s), under conditions and for sufficient time to allow uptake of the polynucleotide, and expressing the polynucleotide in the plant cell(s).

The term "genetically modified" as used herein refers to the introduction of one or more heterologous polynucleotide sequences into one or more plant cells which are part of an intact plant or plant tissue, or which can be regenerated into whole, sexually competent, viable plants. As used herein, the term "heterologous" polynucleotide refers to a sequence that originates from a foreign species, or, if from the same species, is substantially modified from its original form.

A "plant cell" as used herein refers to an intact cell of a leaf, callus, embryo, seed, a gamete producing cell, and any cell which regenerates into a whole plant. Accordingly, a seed comprising multiple plant cells capable of regeneration into a whole plant is included in the definition of a plant cell. The term "intact" as used herein refers to a single cell or group of single cells which form a tissue, wherein the cell(s) have undamaged or untreated cell wall(s). Preferably, the method of the invention is performed using plant tissue comprised of numerous intact cells, rather than using single cells.

As used herein, the term "plant" refers to either a whole plant, a plant part, a plant cell, or a group of plant cells, such as plant tissue, for example. The plant cell treated as described in the method of the invention is considered intact since it has a cell wall which is not removed by enzymatic or other treatment. Preferably the method of the invention is accomplished using a whole plant, however, any intact plant cell(s) or tissue can be used in the method of the invention. Plant discs punched from a leaf are also included in the term "plant". Plantlets, which are typically at the 2–3 leaf stage, are also included within the meaning of "plant". The class of plants which are included in the invention is generally as broad as the class of higher plants amenable to transformation techniques, including both monocotyledonous and dicotyledonous plants. It includes plants of a variety of ploidy levels, including polyploid, diploid and haploid.

As used herein, the term "polynucleotide sequence" or "nucleic acid sequence" refers to a polymer of deoxyribonucleotides or ribonucleotides, in the form of a separate fragment or as a component of a larger construct. DNA encoding the proteins utilized in the method of the invention can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences.

The polynucleotide sequence comprises a nucleic acid sequence comprising at least one structural gene operably associated with a promoter. The term "operably associated" refers to functional linkage between a promoter sequence and the structural gene regulated by the promoter. The nucleic acid sequence, preferably a heterologous sequence, is recombinantly linked or attached to an operably linked promoter, resulting in a chimeric gene. The operably linked promoter controls expression of the polypeptide encoded by the structural gene.

The expression of structural gene coding sequence may be driven by any of a number of promoters, including natural promoters. Although the endogenous promoter of a structural gene of interest may be utilized for transcriptional regulation of the gene, preferably the promoter is a foreign regulatory sequence. For plant expression vectors, for example, viral promoters such as the 35S RNA and 19S RNA promoters of CaMV (Brisson, et al., *Nature*, 310:511–514, 1984; Odell, et al., 1985); the full-length transcript promoter from Figwort Mosaic Virus (FMV) (Gowda, et al., 1989) or the coat protein promoter to TMV (Takamatsu, et al., *EMBO J.* 6:307–311, 1987) may be used. Alternatively, plant promoters such as the light-inducible promoter from the small subunit of ribulose bis-phosphate carboxylase (ssu) (Krebbers, et al., *Plant Mol. Biol.*, 11:745, 1988; Broglie, et al., *Science*, 224:838–843, 1984); mannopine synthase promoter (Velten, et al., 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., *Mol. Cell. Biol.*, 6:559–565, 1986; Severin, et al., *Plant Mol. Biol.*, 15:827–833, 1990) may be used.

Promoters useful in the invention include both constitutive and inducible promoters. The CaMV promoters are examples of constitutive promoters. To be most useful, an inducible promoter should 1) give low expression in the absence of the inducer; 2) give high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.*, 90:4567–4571, 1993); In2-1 and In2-2 regulator sequences which are activated by substituted benzenesulfonamides, e.g., herbicide safeners (Hershey, et al., *Plant Mol. Biol*, 17:679–6990, 1991); and the GRE regulatory sequences which are induced by glucocorticoids (Schena, et al., *Proc. Natl. Acad. Sci., U.S.A.*, 88:10421–10425, 1991). Other promoters, both constitutive and inducible will be known to those of skill in the art.

The particular promoter selected should be capable of causing sufficient expression to result in the production of an effective amount of the structural gene product. The promoters used in the constructs of the present invention may be modified, if desired, to affect their control characteristics.

In addition, tissue specific promoters may be desirable, such as those that are specifically expressed in shoot meristems (Atanassova, et al., *Plant J*, 2:291, 1992) and seed-specific promoters of, for example, *Arabidopsis thaliana* (Krebbers, et al., *Plant Physiol*, 87:859, 1988). Other tissue specific promoters useful in transgenic plants, including the cdc2a promoter and cyc07 promoter, will be known to those of skill in the art. (See for example, Ito, et al., *Plant Mol. Biol*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993).

The structural gene operably linked to a promoter may optionally contain a selectable marker. As used herein, the term "marker" refers to a gene encoding a trait or a phenotype which permits the selection of, or the screening for, a plant or plant cell containing the marker. For example, the marker gene is an antibiotic resistance gene whereby the appropriate antibiotic can be used to select for transformed cells from among cells that are not transformed. Examples of selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance).

Other markers include phenotypic markers such as the GUS gene (β-glucuronidase) (Gallagher, *GUS Protocols: Using the GUS gene as a Reporter of Gene Expression*, Academic Press, San Diego, Calif., 1992), which has an indigo blue gene product when the substrate is X-glu (Jefferson, et al., *EMBO J.*, 6:3901, 1987) or fluorescent with 4-MUG substrate (Jefferson, et al., supra). The "green gene" or green fluorescent protein, GFP, (Inouye and Tsuji, *FEBS Lett.*, 341:277, 1994) expression can be detected by UV light. Other suitable markers will be known to those of skill in the art (see for example, *Current Protocols in Molecular Biology*, Ausubel, et al., John Wiley & Sons, Inc., 1994, Unit 9.6.7). These markers can be used in conjunction with another gene of interest, or can be used alone to optimize parameters for a particular type of plant.

The method of the invention includes monocotyledonous and dicotyledonous plants and plant tissue. Monocotyledonous plants include for example, asparagus, field and sweet corn, barley, wheat, rice, sorghum, onion, pearl millet, rye and oats. Examples of dicotyledonous plants include tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

To commence a transformation process in accordance with the present invention, it is first necessary to construct the foreign gene(s) of interest and before introducing them into the plant cell. The details of the construction of the vectors containing such heterologous genes as described herein are known to those skilled in the art of plant genetic engineering. As used herein, the term "transformation" means alteration of the genotype of a host plant by the introduction of a nucleic acid sequence.

These constructs can be introduced into plant cells using Ti plasmids, root-inducing (Ri) plasmids, plant virus vectors, for example. (For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9, and Horsch, et al., *Science*, 227:1229, 1985, both incorporated herein by reference). The method of the invention utilizes electroporation to introduce DNA into an intact plant.

One of skill in the art will be able to select an appropriate vector, with the minimal requirement being that the introduced nucleic acid sequence be introduced in a relatively intact state. Thus, any vector which will produce a plant carrying the introduced nucleic acid sequence should be sufficient. Even a naked piece of nucleic acid or polynucleotide would be expected to be able to confer the properties of this invention, though at lower efficiency. The selection of the vector, or whether to use a vector, is typically guided by the method of transformation selected, e.g., electroporation.

To be effective once introduced into plant cells, the vector construction including a gene of interest must, in addition to a heterologous gene coding for the protein of interest contain a promoter which is effective in the plant cells to cause transcription of the gene of interest and a polyadenylation sequence or transcription control sequence also recognized in the plant cells. It is also preferred that the plasmid harboring the foreign gene of interest also contain therein one or more selectable marker genes so that the transformed cells can be selected from non-transformed cells in culture, as described herein.

All plant cells which can be transformed by the method of the invention and whole plants regenerated from the transformed cells can be transformed by several different methods, including, but not limited to transformation of cells or tissues with a polynucleotide sequence of interest of seeds, apices, leaves or meristems.

The method of the invention requires contacting an intact plant cell, having a cell wall, with a nucleic acid sequence or polynucleotide as described above, and applying an electrical impulse(s) via electroporation to the plant cell(s), under conditions and for sufficient time to allow uptake of the polynucleotide. Although optimal electroporation conditions will differ slightly with different cell types or different plant types, general methods as described in Fromm, et al., (*Proc. Natl. Acad Sci., U.S.A.*, 82:5824, 1985, incorporated herein by reference) or in the examples herein can be utilized. Optimal conditions can be determined by those of skill in the art with routine experimentation.

Plant tissues, such as a leaf, are electroporated in the presence of plasmids or nucleic acids containing the relevant genetic construct. Electrical impulses of high field strength reversibly permeabilize membranes allowing the introduction of the polynucleotide or plasmid. Wherein electroporated plant protoplasts reform the cell wall, divide and form a plant callus, the method of the invention does not require in vitro culture of the treated plant tissue. Selection of the transformed plant cells with the transformed gene can be accomplished using phenotypic markers such as gus (β-glucuronidase) or NTII (neomycin phosphotransferase) as described above.

Cauliflower mosaic virus (CaMV) may also be used as a vector for introducing the foreign nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired DNA sequence into the unique restriction site of the linker. The modified viral portion of the recombinant plasmid is then excised from the parent bacterial plasmid, and used to inoculate the plant cells or plants.

As used herein, the term "contacting" refers to any means of exposing the polynucleotide or polypeptide to the plant cell. For example, a leaf or other portion of a plant can be immersed or bathed in an electroporation buffer solution containing the polynucleotide or polypeptide to be introduced into the plant. Alternatively, the polynucleotide or polypeptide can be contacted with the intact plant cell by an aerosol spray. Other means of exposing the leaf or intact plant cell to the molecule to be introduced to the plant will be known or readily ascertainable by those of skill in the art. The contacting may be either before or after application of electric impulse(s) via electroporation.

The method of the invention utilizes electroporation as a means for delivering electrical impulse(s) to an intact plant cell or tissue. Electroporation in some or all of the cells in a region of a tissue is caused by short, high voltage electrical pulses applied to the tissue surface or to an underlying tissue region resulting in a transient state of increased tissue permeability. Therefore, as used herein, the term "electroporation" refers to increased permeability of a cell membrane and/or at least a portion of cells of a targeted tissue, wherein the increased permeability is caused by application of voltage across the cell or at least a portion of the tissue. Therefore, square wave pulses, exponential waves, unipolar oscillating wave forms of limited duration, bipolar oscillating wave forms of limited duration, or other wave forms generating electric fields.

Electroporation of intact plant tissue such as a stem or leaf, can be performed either on a region of the whole, intact plant (no cutting or removing a plant part; see FIG. 4), or on a plant tissue which has been removed from the whole plant (e.g., a leaf or an embryo). In addition, plant "discs" or small pieces of the plant can be removed from the plant and "stacked" on top of each other at a total thickness of about 1.5–3.0 mm, preferably about 2 mm, and pulsed as described herein and exemplified in the EXAMPLES.

The composition of the electroporation buffer is not believed to be critical, and generally, conventional electroporation buffers can be used (Fromm, et al., supra). The method of the invention does not require any cell wall-degrading enzyme (e.g., pectin-degrading) in the buffer, nor does it require any lipophilic or other carriers. In addition, it is not necessary to include nuclease inhibitors, such as spermine or other polycations (e.g., spermidine), in the electroporation buffer.

Electric impulses delivered by electroporation include square wave pulses, exponential waves, unipolar oscillating wave forms of limited duration, bipolar oscillating wave forms of limited duration, or other wave forms generating electric fields. Preferably, when a molecule such as a polynucleotide or polypeptide is introduced into the plant cell, the electric impulse is a square wave or an exponential wave. Those of skill in the art will know of apparatus which deliver a desired waveform. For example, a BTX T 820 generator delivers square wave pulses, whereas an ECM 600 generator delivers exponential waves (both available from BTX, Inc. San Diego, Calif.). Needle, pincer, caliper and any other suitable electrodes are used in the method of the invention for delivery of the electric impulse(s). The electrodes are positioned in the region of the plant tissue to be treated. Typically, the number of pulses sufficient to cause electroporation is in the range of 1 to 100, and most preferably between 1 and 50.

The voltage applied between the at least first and second electrode is sufficient to cause electroporation of the intact plant cell(s)/tissue and thereby allow migration of the molecule to be introduced across the cell wall. Preferably, the amount of voltage applied between the electrodes is in the range of about 10 volts to 3000 volts, and preferably from about 50 to 1500 volts.

The voltage setting is dependent on the resistance readings obtained when the electrodes are applied (e.g., needles inserted). For "hard and thick" leaves (e.g., persimmon), the voltages may vary between 1000 and 2500 volts, 8 pulses, 99 μs each, at 1 second intervals. For "soft and thin" leaves, best results may be at lower voltages (e.g., 100–500 volts) and 8–10 ms, spaced 1 second apart. The field strength is calculated by dividing the voltage by the distance (calculated for 1 cm separation; expressed in cm) between the electrodes. For example, if the voltage is 500 V between two electrode faces which is ½ cm apart, then the field strength is 500/(½) or 1000 V/cm or 1 kV/cm.

The electric field strength of the electrical impulse applied is from about 1 to 30 kV/cm and preferably from about 1 to 15 kV/cm. The pulse length is from about 1 microsecond to 100 milliseconds, and preferably from about 1 microsecond to 20 milliseconds.

One of skill in the art could determine the appropriate parameters for the leaf type used. "Soft and thin" leaves, such as petunia are electroporated at low voltage and long pulse length (in ms) (e.g., 40–50V/cm and 50 ms, respectively); "hard and thick" leaves would have higher field strength and shorter pulse length (e.g., 99 μs or less).

In addition, the invention provides a method for producing a heterologous polypeptide in an intact plant cell(s) comprising contacting the plant cell(s) with the polypeptide to be introduced, wherein the introduced polypeptide is biologically active, applying an electrical impulse via electroporation to the plant cell(s), under conditions and for sufficient time to allow uptake of the polypeptide, and recovering the polypeptide in the plant cell(s).

The method has essentially been described above with reference to a method for producing a genetically modified plant by introducing a polynucleotide. The polypeptide introduced is biologically active and has a molecular weight from about 40 kD to 40,000 kD. Depending on the polypeptide to be introduced, suitable biological assays are performed to measure uptake and activity of the introduced polypeptide.

For example, selectable markers can be introduced into the plant cell to measure uptake of any polypeptide. Suitable markers include but are not limited to horseradish peroxidase (as described in the examples herein, 40 kD); carbonic anhydrase (29 kD); phosphorylase b (97.4 kD); beta-galactosidase (116 kD); and alkaline phosphatase (58 kD monomer; 116 kD dimer; 240 kD polymer, etc). The appropriate assays for transformants having a polypeptide introduced will be known to those of skill in the art, depending on the marker utilized.

The method of the invention includes growing a plant from one or more intact plant cells in the situation where a whole plant or leaf is not utilized for the transformation process. For example, the method of producing a polypeptide in a plant includes introduction of a polypeptide into a plant cell having a cell wall. Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a callus or tissue part). The method of the invention does not require dissociation of a plant tissue into cell aggregates or dissociation into single cell suspension. Those of skill in the art will be able to determine appropriate plant types and appropriate plant parts which are amenable to treatment according to the method of the invention, as well as those plants which are capable of regeneration from plant parts.

After treatment of a plant tissue that is not a whole plant, the tissue is transferred to culture media for regeneration. The culture media for growth of plant cells will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al., 1985, supra., after transformation, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained thereby, and propagated vegetatively for commercial use.

In seed propagated crops, the mature transgenic plants are self crossed to produce a homozygous inbred plant. The inbred plant produces seed containing the newly introduced foreign gene(s). These seeds can be grown to produce plants that would produce the selected phenotype.

Parts obtained from the regenerated plant, such as flowers, seeds, leaves, branches, fruit, and the like are included in the invention, provided that these parts comprise cells that have been transformed using electroporation as described. Progeny and variants, and mutants of the regenerated plants are also included within the scope of the invention, provided that these parts comprise the introduced polynucleotide sequences.

The invention includes a plant produced by the method of the invention, including plant tissue, seeds, and other plant cells derived from the genetically modified plant or the plant which produces a heterologous polypeptide.

The invention also provides a method of modulating gene expression in an intact plant, comprising contacting plant cell(s) of the plant with a modulatory amount of polynucleotide applying an electrical impulse via electroporation to the plant cell(s), under conditions and for sufficient time to allow uptake of the polynucleotide and modulating gene expression in the plant. As used herein, the term "modulating" refers to suppressing or enhancing the expression of a gene. Preferably, the method of the invention is used for suppression of gene expression in a plant.

Examples of polynucleotides which are useful for suppressing gene expression include antisense, triplex agents and ribozymes. This approach uses the polynucleotides to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target plant cell(s). The use of antisense methods to inhibit the in vitro translation of genes is well known in the art (Marcus-Sakura, *Anal.Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anti-cancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The embodiments described herein describe the introduction of molecules, such as polynucleotides and polypeptides, into intact plant cells and intact plants, using electroporation. The methods are useful to transfer antisense and other polyucleotides into intact plant leaf and tissue, which can be used as a source of available biopharmaceuticals, but also to incorporate into intact plants recombinant DNA (rDNA) which, on expression, will yield the desired proteins. Plants which are produced by the methods of the invention may provide a source for producing large quantities of monoclonal antibodies, for example.

The polynucleotides or polypeptide compounds are introduced into a plant cell in the form of solutions or sprays, in which either the leaf or the tissue can be dipped in or sprayed with, before or after electroporation. The leaf, in particular, can be considered analogous to a respiratory pathway with already available channels and it is expected that it would be easier to deliver antisense, oligonucleotides and rDNA intracellularly in such a system whereas, for mere stability, it might be more appropriate to electroporate tissues, such as plant callus, with needle electrodes, for example. The methods of the invention can be employed to incorporate specific flavor into plants which can be regenerated and clonally propagated. The plasmid with the appropriate gene can be constructed by any of the conventionally available means and electroporated into plant tissues as described herein.

The methods of the invention are also useful in the development of vaccines. For example, plant-made proteins which can be used as "edible vaccines", will stimulate the recipient's immune system similar to standard active vaccination strategies. Alternatively, an effective immunization strategy may include passive vaccination, where the plant is genetically modified to produce protective antibodies. Therefore, the method of the invention may include introduction of an antigen into the plant cell, either directly, or by a polynucleotide encoding the antigen. Once the leaf or plant containing the antigen is ingested, the antigen may induce an immune response.

The following examples are intended to illustrate but not limit the invention. While they are typical of those that might be used, other procedures known to those skilled in the art may alternatively be used.

EXAMPLE 1

Transient Expression Of Genes In Plant Embryos

The following example illustrates transient gene expression (TGE) of β-glucuronidase (gus), chloramphenicol acetyl transferase (cat), and green fluorescent protein (GFP) genes after transfer into intact maize tissues by electroporation.

One of the objectives of the gene transfer into plants is to regenerate plants with specific characteristics of the plant tissue into which gene has been inserted and expressed. Using a BTX caliper electrode together with an exponential pulse generator, gus gene was transferred into old and relatively larger size embryos.

This experiment was extended to introduce genes into maize tissues with both small and large tissue sections which can be put in an electroporation cuvette with the appropriate genes and pulsed to facilitate gene uptake and their consequent expression. Plant tissues were placed in cuvettes for sterility purposes only.

Maize plants were grown in the green house under standard conditions, and the ears were hand pollinated. Ten to fifteen days thereafter the ears were harvested, surface sterilized in 75% ethanol (10 min), and then rinsed in distilled water twice for 15 minutes each time.

The embryos from the fresh ears were isolated, and a transverse cut was made across the tips of the kernel. The embryos were hand-picked using a sterile dissecting knife. The embryos were further sterilized in 75% ethanol, followed by air drying, and rinsed once with sterile distilled water. Whenever embryos were stored, they were kept in sterile liquid MS media (Murashige and Skoog, *Physiol. Plant*, 15:473, 1962) until ready for use.

Ten to twenty immature embryos (no pretreatment with enzyme) were placed in a 2 mm cuvette with 200 µl of electroporation buffer (EPR), containing 80 mM KCl, 5 mm $CaCl_2$, 10 mM Hepes and 0.42M mannitol, pH 7.2 (D'Halluin, K. et al., *Plant Cell*, 4, 1495–1505, 1992). The embryos were left on ice for 3 hours and then approximately 20–40 µg of plasmid DNA (PBI221 gus) (Clontech, Palo Alto, Calif.) was added to the cuvette just before electroporation. The parameters of electroporation were as follows: a field strength of 2.25 kV/cm and a single pulse of approximately 10 ms, using the BTX 600 exponential wave form generator. One of skill in the art can determine the appropriate voltage, depending on the distance between the electrodes (e.g., with a field strength of 2.25 kV/cm and a 2 mm cuvette, the voltage would be 440 V).

The embryos were left on ice for one hour after electroporation, followed by incubation of the embryos at 37° C. X-glu staining assay was performed as described to examine gus gene expression (Jefferson, et al, *EMBO J.*, 6, 3901–3907, 1987). Briefly, the x-glu histochemical stain was added to the embryos after 24 hours and the stained embryos incubated for another 24 hours at 37° C., before scoring for gus activity. Scoring was performed by microscopic examination based on the entire cell staining blue.

The parameters for introduction of gus gene into intact plants are shown in Table 1.

TABLE 1

| Type of Generators | Field Strength | Pulse Length | # of Pulses |
|---|---|---|---|
| Exponential pulser (BTX ECM 600) | 2.25 kV/cm | 8–12 ms | 1 |
| Square wave pulser | 2.25 kV/cm | 40 µs | 1 |

Electroporation of both immature and mature zygotic embryos, using a BTX ECM 600 exponential pulser with pBI221 gus plasmid, resulted in transient expression of GUS activity in the embryo tissue. The gus gene experiment was repeated using the cat gene and the GFP gene and similar results were obtained. In addition, similar results were obtained with maize using a BTX T820 square wave generator (Table 1).

For cat gene expression, a standard cat assay using thin layer chromatography and radioactively labeled chloramphenicol was utilized (*Current Protocols in Molecular Biology*, supra, Unit 9.6.5). For GFP gene expression, the following parameters were utilized: BTX ECM 600 exponential pulser; 325 V; pulse length, 2 ms; resistance reading: 246 ohm). After pulsing, the embryo was placed on MS media and cultured for 24 hours at 37° C. Under UV light, the culture fluoresced green, indicating gene expression (*Current Protocols in Molecular Biology*, supra, Unit 9.6.10).

Such direct introduction of DNA allows plants to be grown directly from the transformed embryos by standard methods known to those of skill in the art. This technique avoids the problem of protoplast regeneration and relatively long periods of tissue culture typically required in plant transformation techniques.

EXAMPLE 2

Electroporation Of Persimmon Leaf And Incorporation Of Horserradish Peroxidase The following example shows the incorporation of horseradish peroxidase (HRP) directly into an intact leaf, after electrical impulse is applied to the leaf. Briefly, untreated leaves of persimmon plants were pulsed using needle electrodes connected to a BTX T 820 generator (BTX, Inc., San Diego, Calif.). This apparatus delivers square wave pulses whose number, intensity and length can be varied by pre-setting values on the front panel of the instrument, and a BTX Optimizor®, which displays resistivity of the test sample and also the shape and parameters of the pulses delivered.

The distance between the needles was set to 5 mm, however this distance can be varied over a wide area depending on the area to be treated. After pulsing, a 5 mm square was excised from the leaf and dipped into EPR solution (EXAMPLE 1) containing HRP protein marker (FIG. 1).

The parameters for electroporation were as follows: 8 pulses (a range of 4–16 is sufficient); pulse length: 99 $\mu$s (50 $\mu$s to 3 ms range); voltage 1000 V to 2500 V (see specification for voltage range depending on thick or thin leaf).

In a second set of experiments, needle electrodes were replaced by pincer type of electrodes, which also allows in planta electroporation in an intact leaf (FIG. 2). As described above, the field strength can be varied over a range depending on a thick or thin plant sample and polypeptide marker. It would be a matter of routine to optimize parameters to give the best uptake for each plant type or cell type and each polypeptide, depending on molecular weight of the polypeptide.

For use of the pincer type electrodes, an area of 5 mm square was excised from the leaf and put between the pincer electrodes which are made of gold, connected by wires. For prevention of sparks, a 1 mm thick silicon wall was put around the gold electrodes. The lower electrode has a receptacle 10 mm in diameter which is filled with appropriate polypeptide markers which have no ions. The leaf was then pulsed as described below.

| Resistance: | 400 Ω | Field Strength: | 400 V/cm |
|---|---|---|---|
| Pulse length: | 99 $\mu$s | # pulses: | 8 |

The results of several experiments performed using intact leaves with either needle or pincer type electrodes are shown below and were based on a standard biochemical assay for HRP (ABTS peroxidase substrate system (Kirkgaard & Perry, Gaithersburg, Md.) was added for color development). The uptake is based on a visual comparison of color.

| | Applied voltage | | |
|---|---|---|---|
| | 50 V | 1000 V | 2500 V |
| Needle | − | + | ++ |
| Pincer | − | + | ++ |

− no uptake
+ good uptake
++ very good uptake

The leaves' cell walls were examined after two weeks and shown to take up and integrate and enzyme into the cell, as seen by changes and intensity of the color developed.

With regard to electroporation of intact leaf and tissue, sterility conditions are easier to implement when electroporated in the cuvette. However, the technique described for in situ, in vivo electroporation of leaf can be very easily accomplished in a sterile atmosphere. The methodology described herein allows regeneration and clonal propagation of plants.

EXAMPLE 3

Introduction Of Genes Into Whole, Intact Plants

As shown in FIGS. 3a–3e, the methods described in EXAMPLES 1 and 2 were followed using intact, whole plants (persimmon). The parameters described above were followed and plant leaves were either dipped into a solution containing gus gene, or the solution was directly applied (e.g., to the stem). Alternatively, a solution containing the gene or polypeptide of interest, could be applied by aerosol spray, prior to or concomitantly with electroporation.

Following electroporation directly on the intact plant leaf or stem, gene expression (gus) was confirmed by the x-glu assay described in EXAMPLE 1. The results show that it is not necessary to cut a plant into small pieces or dissociate the cells at all, in order to effectively introduce DNA into the plant.

EXAMPLE 4

Electroporation Of Stacked Leaf Tissue

The following experiment shows that multiple pieces of tissue can be electroporated at one time, increasing the efficiency of transfer of a polynucleotide. Briefly, an intact leaf, either "hard and thick" or "soft and thin" type (as previously described herein), including the stem of the leaf, was cut and placed in a container (stem first), which included plasmid DNA in EPR buffer. The leaf was incubated for approximately 1–2 hours at room temperature (see illustration in FIG. 4a) to allow uptake of DNA into the leaf. For exemplary purposes, petunia (soft and thin) was utilized in this example.

Figure 4A:
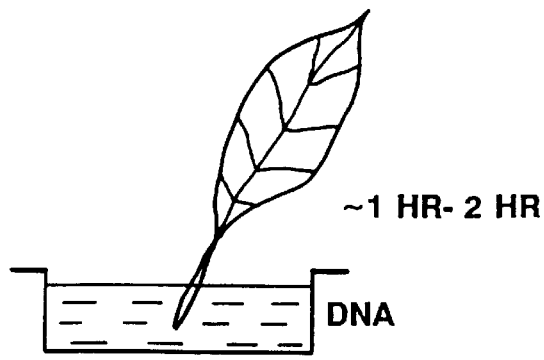
FIG. 4a shows treatment of a leaf in EPR buffer
Figure 4B:
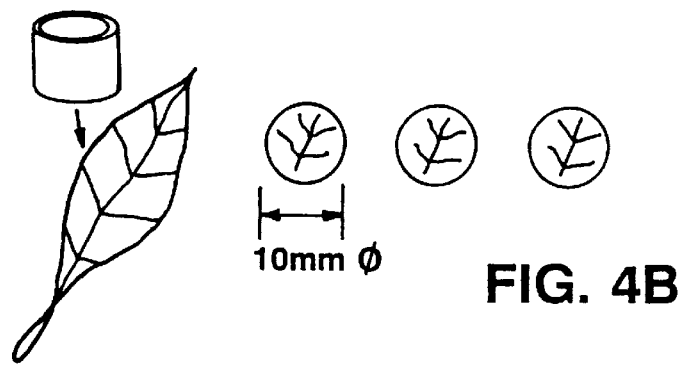
FIG. 4b shows leaf punches.
Figure 4C:
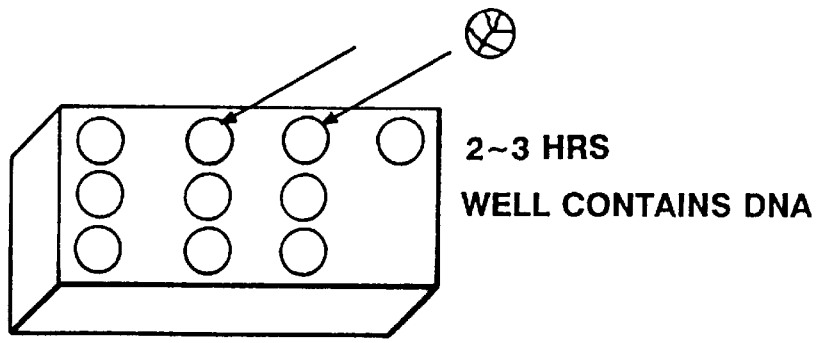
FIG. 4c shows placement of leaf discs into a microtiter plate.

Following incubation, approximately 10 mm size (diameter) sections of leaf tissue were punched out (e.g., with a paper hole puncher) (see illustration in FIG. 4b). The individual pieces were placed in a 24 well plate (sterile) with the same DNA solution as above and incubated for 2–3 hours (FIG. 4c).

Figure 4D:
FIG. 4d shows stacking of leaf discs.
Figure 4E:
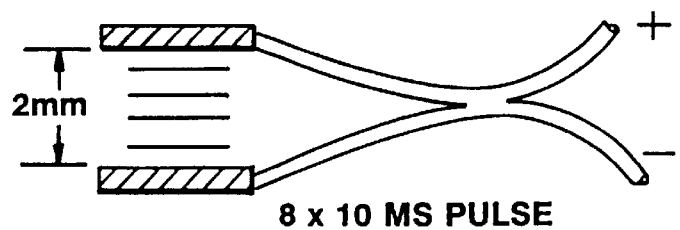
FIG. 4e shows pulsing of leaf discs.

The individual leaf pieces were removed and stacked in layers of 5–6 pieces, or approximately 2 mm. The stack was placed between pincer type electrodes, however, caliper, pincer, or other electrodes would give similar results. The number of leaves in the stack is preferably greater than 2 so as to prevent arcing or hole formation (FIG. 4d). In this particular experiment, a T820 electroporator was used, preferably in the low voltage (LV) mode. The stacks were pulsed approximately 8 times at 10 ms each (FIG. 4e). If the field strength is too high (e.g., 250 V/2 mm), the leaves may change color, indicating damage. One of skill in the art would readily recognize such an occurrence. Preferably, the voltage was optimal at 150 V and 50 V/2 mm. The field strength should preferably not be greater than 500 V/cm.

One of skill in the art could determine the appropriate parameters for the leaf type used. "Soft and thin" leaves, such as petunia are electroporated at low voltage and long pulse length (in ms) (e.g., 40–50 V/cm and 50 ms, respectively); "hard and thick" leaves would have higher field strength and shorter pulse length (e.g., 99 $\mu$s or less).

After electroporation, the leaves were incubated for 15 minutes, followed by electroporation once or twice more (with 15 minute intervals). For uptake of DNA, gene expression was measured using the x-glu assay system (gus gene) and observation of blue cells (see EXAMPLE 1). The plant cells in the entire leaf disc expressed the gus gene, and not just the cells on the periphery of the disc. Therefore, it is not necessary to expose cells by cutting or dissociating prior to DNA uptake and electroporation.

The above experiment was repeated using corn tissue and a caliper electrode (BTX, San Diego, Calif.). The stack of tissue was approximately 2 mm thick and the tissue was pulsed about 5 times at 8 ms each. In three separate experiments at a voltage of 50 V, 100 V and 150 V, there was no difference in the extent of incorporation of the gene. All three voltages resulted in uptake and expression of gus gene, as determined above.

EXAMPLE 5

Transformation of Lettuce (*Lactuca sativa*) Mediated By *Agrobacterium tumefasciens* And Electroporation Transformation of intact plants was compared using conventional *Agrobacterium tumefasciens* as a means of transformation versus the electroporation method of the present invention. These studies were performed using cv. Cobham Green (Syn. Dark Green Boston) since previous studies have shown adequate rates of regeneration with this cultivar. Seeds were surface sterilized by dipping them in 75% ethanol for 15 seconds followed by 60 minutes in 25% Chlorox with a trace of Tween 20 detergent, and then two washes in sterile distilled water. The seeds were plated onto 1.0% agar containing half strength Hoaglands solution and 10 $\mu$g/ml GA$_3$. Seeds were incubated in a growthroom at 29° C. After four days the cotyledons were cut with a scalpel into two pieces and used in the transformation experiment with *Agrobacterium tumefasciens*. In the electroporation experiment, the cotyledons were grown for six days in order to obtain larger leaf sizes. Circular leaf discs (about 6 mm in diameter) were then cut out from the cotyledons using a #2 corkborer. The circular leaf discs were used for all electroporation studies.

In plant transformation experiments, plasmid pBI121 (Clonetech), and plasmids pMON120, pMON200, pMON505, pMON530, and pMON9749 (Monsanto Co.) were used. For the present studies, plasmid pMON9749 in *A. tumefasciens* strain ASE was used for the Agrobacterium-mediated transformation experiment, and plasmid pBI121 (gus) was used for the electroporation experiment.

All transformation experiments employed tobacco nurse cultures. Three ml of a log phase cell suspension culture of *Nicotiana plumbaginifolia* was pipetted onto 1.0% agar plates containing NT medium two days before the transformation experiments and incubated in a growth chamber at 29° C. Just prior to the transformation experiments, filter paper discs (Whatman #2) were laid over the nurse cultures.

Transformed plant material was initially placed on top of the filter paper and cocultivated in a growth chamber at 29° C. for two days. Previous studies have shown that while the "co-cultivation" in the presence of a nurse culture (Nicotians) was not absolutely necessary, with Lactuca, a nurse culture is beneficial to ensure predictable high rates of transformation. It appears that exudates from the tobacco cells can minimize stress and promote growth. It has also been suggested that compounds from the tobacco cells stimulate the vir genes in *A. tumefasciens*.

Agrobacterium Mediated Transformation

Cut cotyledons were soaked in a suspension of *A. tumefasciens* (5×10$^8$ bacteria/ml) for 10 minutes, blotted on filter paper to remove excess suspension, and placed on the nurse cultures for two days. After cocultivation, the explants were plated on SH medium (callusing medium) containing the growth regulators indolacetic acid (IAA, 1 mg/l) and kinetin (KIN, 0.5 mg/l). Previous experiments have shown that the optimal regime appears to be culturing for about 12 days on callusing medium (with growth regulators) followed by subculturing on regeneration medium (SH; KIN 0.05 mg/l; zeatin 0.05 mg/l). After co-cultivation, all media contained the antibiotics kanamycin (50 mg/ml) and carbenicillin (500 mg/ml) (Note: callus formation occurs mostly along the cut edges of the cotyledons).

Electroporation

Circular leaf discs were place in individual wells in a sterile 96-well microtiter plate containing 75 ul of a plasmid solution (pBI121 in 10% glycerol) and incubated for 3 hours. The experiment was performed with two separate plasmid concentrations, 50 ug/ml and 100 ug/ml, and with circular or linearized pBI121. The leaf discs were then stacked in 6–7 layers, place between the BTX caliper electrodes (the electrodes spacing was about 2 mm), and electroporated in the LV mode (8 pulses for 10 milliseconds each) at voltages of 250 v/cm, 500 v/cm, and 750 v/cm. After electroporation, some of the leaf discs were placed back in the plasmid solution for 15 minutes and then re-electroporated with similar conditions. The re-electroporation was repeated once or twice (indicated below as 2 cycles or 3 cycles). The parameters of the experiments are shown in Table 2 below:

TABLE 2

|    | Plasmid conc. ($\mu$g/l) | Type of Plasmid | Voltage V/cm | # of cycles |
|----|---------|----------|-----|---|
| 1. | 50  | circular | 250 | 1 |
| 2. | 50  | circular | 250 | 2 |
| 3. | 50  | circular | 250 | 3 |
| 4. | 50  | linear   | 500 | 1 |
| 5. | 50  | linear   | 500 | 2 |
| 6. | 50  | linear   | 500 | 3 |
| 7. | 100 | circular | 250 | 1 |
| 8. | 100 | circular | 250 | 2 |

TABLE 2-continued

|   | Plasmid conc. (μg/l) | Type of Plasmid | Voltage V/cm | # of cycles |
|---|---|---|---|---|
| 9. | 100 | circular | 500 | 1 |
| 10. | 100 | circular | 500 | 2 |
| 11. | 100 | circular | 750 | 1 |
| 12. | 100 | circular | 750 | 2 |

The efficiency of transfer of DNA using Agrobacterium versus electroporation is compared after callus formation or regeneration of the leaf disks, respectively.

Although the invention has been described with reference to the presently preferred embodiment, it should be understood that various modifications can be made without departing from the spirit of the invention. Accordingly, the invention is limited only by the following claims.

We claim:

1. A method of producing a genetically modified plant, the method comprising:
   contacting intact plant tissue with a polynucleotide wherein the polynucleotide is operably associated with a promoter;
   applying a pulsed electrical field via electroporation to the plant tissue, under conditions and for sufficient time to allow uptake of the polynucleotide, wherein the length of the electrical impulse applied is from about 1.0 μsec to 20 msec and wherein the plant tissue is not pretreated with a cell membrane-penetrating agent or a lipophilic agent; and
   expressing the polynucleotide in cell(s) of the tissue.

2. The method of claim 1, wherein the plant tissue is selected from the group consisting of a gamete producing cell, leaf, callus, embryo, seed, and any cell which regenerates into a whole plant.

3. The method of claim 1, wherein the promoter is a constitutive promoter.

4. The method of claim 1, wherein the promoter is an inducible promoter.

5. The method of claim 4, wherein the promoter is induced by chemical means.

6. The method of claim 1, wherein the polynucleotide encodes at least one structural gene.

7. The method of claim 6, wherein the structural gene is an antigen.

8. The method of claim 1, wherein the plant tissue is derived from a dicotyledonous plant.

9. The method of claim 1, wherein the plant tissue is derived from a monocotyledonous plant.

10. The method of claim 1, wherein the polynucleotide further comprises a selectable marker.

11. The method of claim 1, wherein the electrical impulse(s) is comprised of square wave pulses, exponential waves, unipolar oscillating wave forms of limited duration, bipolar oscillating wave forms of limited duration, or other wave forms generating electric fields.

12. The method of claim 11, wherein the electrical impulse(s) is comprised of square wave or exponential wave pulses.

13. The method of claim 1, wherein the voltage of the electrical impulse applied is from about 10 to 3000 V.

14. The method of claim 1, wherein the field strength of the electrical impulse applied is from about 1.0 to 15.0 kV/cm.

15. The method of claim 1, wherein the polynucleotide is in an expression vector.

16. The method of claim 15, wherein the vector comprises a T-DNA derived vector.

17. A method for introducing a heterologous polypeptide into intact plant tissue comprising:
   contacting the plant tissue with the polypeptide to be introduced, wherein the introduced polypeptide is biologically active;
   applying a pulsed electrical field via electroporation to the plant tissue, under conditions and for sufficient time to allow uptake of the polypeptide into the cells of the tissue; and
   recovering the polypeptide from the plant tissue.

18. The method of claim 17, wherein the plant tissue is selected from the group consisting of a gamete producing cell, leaf, callus, embryo, seed and any cell which regenerates into a whole plant.

19. The method of claim 17, wherein the polypeptide has a molecular weight from about 40 kD to 40,000 kD.

20. The method of claim 17, wherein the plant tissue is derived from a dicotyledonous plant.

21. The method of claim 17, wherein the plant tissue is derived from a monocotyledonous plant.

22. The method of claim 17, wherein the electrical impulse(s) is comprised of square wave pulses, exponential waves, unipolar oscillating wave forms of limited duration, bipolar oscillating wave forms of limited duration, or other wave forms generating electric fields.

23. The method of claim 22, wherein the electrical impulse(s) is comprised of square wave or exponential wave pulses.

24. The method of claim 17, wherein the voltage of the electrical impulse applied is from about 10 to 3000 V.

25. The method of claim 17, wherein the field strength of the electrical impulse applied is from about 1 to 15 kV/cm.

26. The method of claim 17, wherein the length of the electrical impulse applied is from about 1 μsec to 20 msec.

27. A method of modulating gene expression in intact plant tissue, comprising:
   contacting plant tissue with a modulatory amount of polynucleotide;
   applying a pulsed electrical field via electroporation to the plant tissue, under conditions and for sufficient time to allow uptake of the polynucleotide; and
   modulating gene expression in the plant tissue.

28. The method of claim 27, wherein the polynucleotide is selected from the group consisting of antisense, triplex agent and ribozyme.

29. The method of claim 27, wherein the plant tissue is selected from the group consisting of a gamete producing cell, leaf, callus, embryo, seed, and any cell which regenerates into a whole plant.

30. The method of claim 27, wherein the modulating is suppression of gene expression.

* * * * *